US00PP27547P3

(12) United States Plant Patent
Layt

(10) Patent No.: US PP27,547 P3
(45) Date of Patent: Jan. 17, 2017

(54) ***CALLISTEMON VIMINALIS* PLANT NAMED 'LJ23'**

(50) Latin Name: *Callistemon viminalis*
Varietal Denomination: LJ23

(71) Applicant: Todd Anthony Layt, Clarendon (AU)

(72) Inventor: Todd Anthony Layt, Clarendon (AU)

( * ) Notice: Subject to any disclaimer, the term of this patent is extended or adjusted under 35 U.S.C. 154(b) by 533 days.

(21) Appl. No.: 13/986,727

(22) Filed: May 29, 2013

(65) Prior Publication Data

US 2014/0359908 P1 Dec. 4, 2014

Related U.S. Application Data

(60) Provisional application No. 61/658,465, filed on Jun. 12, 2012.

(51) Int. Cl.
*A01H 5/00* (2006.01)

(52) U.S. Cl.
USPC ..... Plt./226

(58) Field of Classification Search
USPC ..... Plt./226, 263.1
CPC ..... A01H 5/02; A01H 5/00
See application file for complete search history.

(56) References Cited

PUBLICATIONS http://www.bestplants.com.au/native-shrubs-groundcovers/green-john.html 2010.*

* cited by examiner

*Primary Examiner* — Kent L Bell
(74) *Attorney, Agent, or Firm* — Samuel R. McCoy, Jr.

(57) ABSTRACT

'LJ23' is a distinctive variety of *Callistemon viminalis* which is characterized by the combination of a dense growth habit, large leaves, and green foliage as well as the stability and uniformity of traits through successive cycles of asexual propagation.

1 Drawing Sheet

Latin name of the genus and species: The Latin name of the genus and species of the novel variety disclosed herein is *Callistemon viminalis.*

Variety denomination: The inventive variety of *Callistemon viminalis* disclosed herein has been given the variety denomination 'LJ23'.

BACKGROUND OF THE INVENTION

The present invention relates to a new and distinct perennial variety of *Callistemon viminalis*, which has been given the variety denomination of 'LJ23'. *Callistemon*, a member of the myrtle family, is a relatively large genus of shrubs and small trees noted for their unique bottlebrush inflorescences which typically cover plants in spring and fall with colors ranging from white to pink to dark red. Nurserymen and plant breeders alike have for several decades made seedling selections for different habits with forms and sizes now ranging from low growing groundcovers to large trees. *Callistemon* is a popular landscape plant in its native Australia as well as in the western and southern United States.

Parentage: *Callistemon viminalis* 'LJ23' was the result of a seedling selection from an openly pollinated plant of *Callistemon viminalis* 'Little John' and was discovered in Clarendon, Sydney, NSW. In 2006 seed was collected from *Callistemon viminalis* 'Little John' plants and many seedlings were grown. Six candidate plants were selected from said seedlings and further grown and evaluated for subsequent testing. In 2009 a final selection took place and one plant was then selected as the final candidate due to the combination of a dense growth habit and large leaves, green foliage. The plant was given the name 'LJ23'.

Asexual Reproduction: 'LJ23' was grown to a mature age and was found to grow uniform; 4 successive cycles of vegetative propagation have proven to be true to type. Propagation was first accomplished in 2009 at a commercial plant breeding facility in Clarendon, New South Wales, Australia using softwood cuttings and roots well without the aid of rooting compound or hormone. Time to develop roots is approximately 2 to 4 weeks and an average crop time is approximately 12 months to produce a mature and marketable 400 mm container, starting from a rooted cutting. 'LJ1' was grown to a mature age and was found to grow uniform; 4 successive cycles of vegetative propagation have proven to be true to type.

SUMMARY OF THE INVENTION

'LJ23' is a distinctive variety of *Callistemon viminalis* which is characterized is by the combination of a dense growth habit and large leaves, green foliage.

BRIEF DESCRIPTION OF THE FIGURES

The figure shows three representative 'LJ23' plants.

BOTANICAL DESCRIPTION OF THE PLANT

The following is a detailed botanical description of a new and distinct variety of *Callistemon viminalis* known as 'LJ23' based upon observations of 3 year old plants grown, in full sun in open landscape beds in Clarendon, New South Wales, Australia. These plants were transplanted into the landscape beds as 200 mm nursery pots grown from rooted cuttings, approximately 24 months prior to field observations. Plants were maintained with granular slow release fertilizer and regularly watered with overhead irrigation. No pest and disease measures were taken. Observation data was recorded in May of 2011.

Those skilled in the art will appreciate that certain characteristics will vary with older or, conversely, with younger plants. 'LJ23' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 2001 edition.

A botanical description of 'LJ23' and comparisons with other varieties of *Callistemon viminalis* are provided below.

Technical Description of the Variety.

Plant description:

*Plant habit*.—Shrub; semi erect, rounded and dense.

*Height*.—Approximately 60 to 100 cm at maturity.

*Width*.—Approximately 60 to 80 cm at maturity.

*Bloom period*.—Spring.

*Hardiness*.—USDA Zone 8 to 11.

*Environmental tolerances*.—Similar to the parent plant; tolerates light shade, a wide range of soil conditions and drought tolerant once established.

*Pest and disease susceptibility or resistance*.—In common with the species, none of note.

Stem:

*Branching and habit*.—Strong branching habit; branch angles acute, branch attitude is erect to semi erect.

*Stem strength*.—Woody and strong.

*Shape*.—Cylindrical.

*Stem surface*.—Immature stems are corky with a smooth texture and light pubescence while mature stems are woody, exhibiting irregular segments of papery texture which are delineated by fissures of varying depth and width.

*Stem color*.—Immature stem appearing as a uniform blend of greyed-yellow RHS 161C and yellow-green RHS 145C. Mature stems exhibit irregular segments of grey brown RHS 199D with fissures which are brown RHS 200D.

*Stem dimensions*.—Freely-branching primary stems arise from a single trunk near soil level with the longest of said primary stems measuring 40 cm long and 1.2 cm in diameter near the base and approximately 1.5 mm at the apex. Secondary branches arise freely at nodes; dimensions of secondary branches are widely varied depending on age.

*Internode length*.—Ranges from 10 to 15 mm.

Foliage:

*Type*.—Evergreen.

*Shape*.—Elliptical.

*Division*.—Simple.

*Apex*.—Mucronate.

*Base*.—Cunneate.

*Venation*.—Pinnate.

*Vein color* (*adaxial surfaces*).—Indistinguishable from the surrounding foliage.

*Vein color* (*abaxial surfaces*).—Indistinguishable from the surrounding foliage.

*Margins*.—Mature margin is entire; immature margin is ciliate.

*Arrangement*.—Alternate.

*Attachment*.—Petiolate.

*Texture*.—Leathery.

*Surfaces* (*adaxial surface*).—Juvenile: medium pubescence; mature: glabrous.

*Surfaces* (*abaxial surface*).—Juvenile: medium pubescence; mature: glabrous.

*Mature leaf dimensions*.—Average length is 48.1 mm and the average width is 9 mm with a length-to-width ratio of 5.34:1.

*Leaf color* (*adaxial surface*).—Juvenile: is 146A; mature: 137A.

*Leaf color* (*abaxial surface*).—Juvenile: is 146A; mature: 137A.

*Petiole*.—Approximately 1 mm in length and less than 1 mm wide; greyed-red 179B in color and pubescent.

*Stipules*.—None observed.

Inflorescence:

*Inflorescence*.—Inflorescences of *Callistemon* are distinguished by their brightly colored, exserted stamen which gives the flower spike a bottlebrush appearance. Spikes are indeterminate and leafy with an overall length of approximately 6 to 10 cm and a width of 5 to 6 cm, comprised of many small sessile florets with exserted stamens.

*Bud*.—Oblong or ovoid axillary buds measuring approximately 6 mm long and 3 mm wide prior to bud swell. Color approximates to yellow-green 146D, prior to bud swell.

*Florets*.—Sessile. Predominant color of exserted stamens red (RHS 45B). Observed length of 13 to 16 mm (average length is 14.2 mm) and very thin in diameter (less than 1 mm). Greater than 40 in number. Sepals are immeasurably minute. Inconspicuous corolla comprised of five cupped, unfused petals; diameter across corolla is approximately 9.6 mm. Color of the corolla approximates to yellow-green (RHS 154C or 154D). Non fragrant.

Reproductive organs:

*Stamens*.—Many; greater than 40.

*Stamen color*.—45B.

*Stamen dimensions*.—Average of 14.2 mm and very thin.

*Attachment*.—Each stamen joins floral tube independently: Free.

*Anther dimensions*.—Minute.

*Anther color*.—Yellow.

*Pollen*.—Present.

*Pistil*.—One.

*Pistil dimensions*.—About 14 mm in length and very thin.

*Pistil color*.—45B.

*Ovary position*.—Half-Inferior.

Fruit and seed production: Dehescent flowers reveal round, slightly oblong seed capsules grouped tightly along the stem. Sessile. Dimensions are 3 to 5 mm in diameter and 4 to 5 mm in length. Color at maturity approximates to brown 200A. Seeds are many and minute with a color close to greyed orange 166B.

Comparisons with Other *Callistemon*

When compared with seed parent *Callistemon viminalis* 'Little John' (unpatented), 'LJ23' has a similar size as 'Little John' but a more dense growth habit and larger, dark green leaves. The leaves of 'LJ23' are, on average, 48.1 mm long and 9 mm wide whereas the leaves of 'Little John' are 38.5 mm long and 8.4 mm wide, on average. 'LJ23' has dark green mature foliage corresponding to 137A whereas the foliage of 'Little John' is closest to 137B.

Plants of the new cultivar 'LJ23' are most comparable to the commercial variety *Callistemon viminalis* 'Matthew Flinders' (U.S. Plant Pat. No. 17,314) in that both varieties exhibit a dwarf habit and green foliage. However, the foliage of 'LJ23' is approximately 50 percent longer and wider than the foliage of 'Matthew Flinders'.

That which is claimed is:

1. A new and distinct variety of *Callistemon viminalis* plant named 'LJ23', substantially as described and illustrated herein.

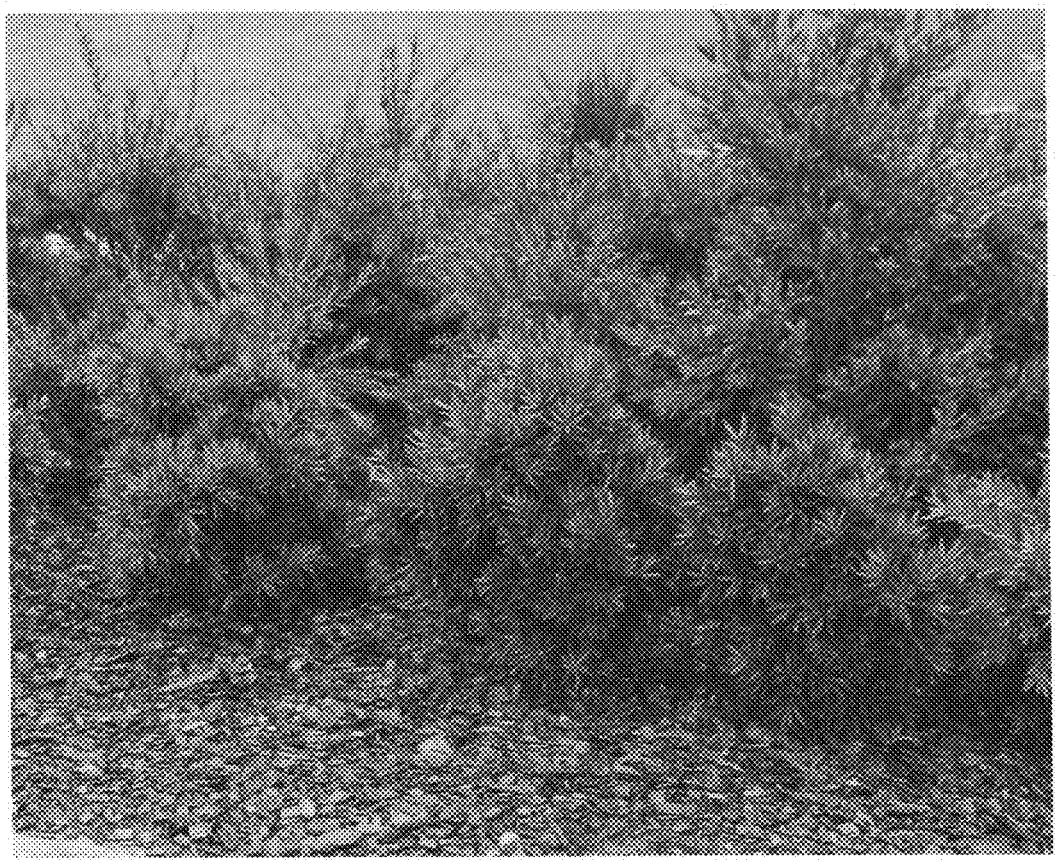

* * * * *